United States Patent [19]

Kimball et al.

[11] Patent Number: 5,697,366
[45] Date of Patent: Dec. 16, 1997

[54] IN SITU CALIBRATION SYSTEM FOR SENSORS LOCATED IN A PHYSIOLOGIC LINE

[75] Inventors: Victor E. Kimball, Burnsdale; Laurie E. Lynch, Eden Prairie; Irvin T. Pierskalla, Robbinsdale, all of Minn.; Christopher H. Porter, Woodinville, Wash.

[73] Assignee: Optical Sensors Incorporated, Minneapolis, Minn.

[21] Appl. No.: 379,332

[22] Filed: Jan. 27, 1995

[51] Int. Cl.$^6$ ............................................. A61B 5/00
[52] U.S. Cl. ............................................. 128/632
[58] Field of Search .................. 128/630–635; 73/1 R; 356/39–42; 364/413.07–413.11

[56] References Cited

U.S. PATENT DOCUMENTS

| | | |
|---|---|---|
| 3,615,709 | 10/1971 | Ford et al. . |
| 3,681,255 | 8/1972 | Wilfore et al. . |
| 3,710,778 | 1/1973 | Cornelius . |
| 3,859,049 | 1/1975 | Ware et al. . |
| 3,892,058 | 7/1975 | Komatsu et al. . |
| 3,895,093 | 7/1975 | Weidenbach et al. . |
| 4,109,505 | 8/1978 | Clark et al. . |
| 4,116,336 | 9/1978 | Sorensen et al. . |
| 4,119,406 | 10/1978 | Clemens . |
| 4,171,288 | 10/1979 | Keith et al. . |
| 4,266,941 | 5/1981 | Sullivan . |
| 4,470,520 | 9/1984 | Sullivan . |
| 4,478,222 | 10/1984 | Koning et al. . |
| 4,535,786 | 8/1985 | Kater ........................... 128/630 X |
| 4,739,645 | 4/1988 | Drbal . |
| 4,759,371 | 7/1988 | Franetzki . |
| 4,786,394 | 11/1988 | Enzer et al. ..................... 128/635 X |
| 4,830,013 | 5/1989 | Maxwell . |
| 4,871,439 | 10/1989 | Enzer et al. . |
| 4,960,708 | 10/1990 | Zowtiak et al. . |
| 5,046,496 | 9/1991 | Betts et al. ....................... 128/635 |
| 5,057,278 | 10/1991 | Maxwell et al. . |
| 5,096,669 | 3/1992 | Lauks et al. .................... 204/409 X |
| 5,165,406 | 11/1992 | Wong ............................. 128/635 |
| 5,325,853 | 7/1994 | Morris et al. . |
| 5,330,634 | 7/1994 | Wong et al. . |
| 5,365,925 | 11/1994 | Lee . |

FOREIGN PATENT DOCUMENTS

WO 94/06019  3/1994  WIPO .

OTHER PUBLICATIONS

U.S. Application Serial No. 07/911,175 to Olstein, filed 12 Aug. 1992.

U.S. Application Serial No. 08/074,749 to Olstein et al., filed 10 Jun. 1993.

*Primary Examiner*—Jennifer Bahr
*Assistant Examiner*—Samuel Gilbert
*Attorney, Agent, or Firm*—Kenneth Barovsky; Bozicevic & Reed LLP

[57] ABSTRACT

A method is provided for calibrating sensors used to analyze characteristics of physiologic fluids such as blood. The method involves the use of a sensor assembly having an analyte-responsive sensor in communication with a passageway which is in divertable fluid communication with a physiologic line and a conduit by which a reference sample may be introduced into the passageway. The method involves exposing the sensor to the reference sample, thereby producing a sensor response. The method also allows performing quality control on the sensors. Also provided is an apparatus with which the claimed method may be practiced.

27 Claims, 2 Drawing Sheets

IN SITU CALIBRATION SYSTEM FOR SENSORS LOCATED IN A PHYSIOLOGIC LINE

TECHNICAL FIELD

This invention relates generally to chemical sensors. More particularly, the invention relates to methods and devices for calibrating sensors used to monitor chemical characteristics of physiologic fluids such as blood.

BACKGROUND

Clinical decisions regarding patient management are often made on the basis of blood chemistry analysis. A variety of procedures have been used to perform such analyses, all of which have their deficiencies.

Blood chemistry is often determined on a drawn sample of blood which is subsequently transported to an on-site facility where the analysis is performed. Blood chemistry analysis performed by such a process engenders a risk of contact with the blood sample, an increased risk to the patient of nosocomial infections and the possibility that air emboli may be introduced into the bloodstream, a potential for contamination of the sample, and, perhaps most significantly from the diagnostician's point of view, a lengthy delay between a decision that blood chemistry is necessary and delivery of therapy based on the results of the analysis.

The need for a bedside system to analyze critical blood variables (e.g., $O_2$, $CO_2$ and pH) has been addressed by placing environment-sensitive, calibrated optical or electrochemical sensors directly into a patient's artery or vein. Intraarterial or intravenous sensors are typically calibrated by immersion in a solution which has been equilibrated by bubbling with known concentrations of, for example, $O_2$ and $CO_2$, to provide a liquid with known partial pressures of $O_2$ and $CO_2$ (i.e., $pO_2$ and $pCO_2$). The ability of the sensors to detect $pO_2$ and $pCO_2$ is then compared with the known $pO_2$ and $pCO_2$; this process is referred to as calibration by tonometry.

A major disadvantage of this system is that once a calibrated sensor is inserted into a patient's blood vessel, it must be removed from the vessel for re-calibration and sterilized again before it can be reinserted. Furthermore, it is equally difficult to perform quality control measurements to determine whether the sensors are functioning properly. Absent the ability to re-calibrate, it is extremely difficult to determine whether the system is performing properly after the sensors have been inserted. In fact, poor performance is frequently seen since (1) intraarterial or intravenous sensors are prone to thrombogenic formations which can cause serious measurement errors and (2) patient movement can result in sensor contact with the vessel wall which can also cause temporary or permanent measurement errors.

An alternative approach is a paracorporeal or extracorporeal system for bedside blood chemistry analysis. The paracorporeal system places the sensors in a physiologic line very near to a patient's arterial catheter. This approach has the primary advantages of eliminating the problems associated with thrombosis and patient movement and, in addition, provides the capability to conduct in situ calibration and quality control checks without compromising sterility.

A paracorporeal design allows for a calibration to be made while the sensors are either in the physiologic line (e.g., arterial or venous line) or removed from the physiologic line (i.e., ex vivo). Moreover, quality control checks may be made at any time throughout the life of the sensors.

Accordingly, novel methods of conducting in situ or ex vivo calibration and quality control testing are provided for use with sensors positioned either in a physiologic line or separate from a physiologic line.

RELATED ART

The following references relate generally to methods and systems for monitoring blood chemistry and/or for calibrating the system used therefor.

U.S. Pat. No. 4,109,505, issued 29 Aug. 1978 to Clark et al., describes a system for analyzing blood for use with an indwelling catheter, whereby automatic blood withdrawal and automatic calibration may be effected.

U.S. Pat. No. 4,119,406, issued 10 Oct. 1978 to Clemens, describes an apparatus used in a calibration system which employs a manifold through which sample and calibrating solutions may be pumped through a sensor.

U.S. Pat. No. 4,739,645, issued 26 Apr. 1988 to Drbal, describes a calibration vial in which a blood gas sensor is stored and calibrated by bubbling gas into the vial.

U.S. Pat. No. 4,830,013, issued 16 May 1989 to Maxwell, describes an apparatus for measuring various parameters of blood using a sensor mounted in an indwelling catheter.

U.S. Pat. No. 4,871,439, issued 3 Oct. 1989 to Enzer et al., describes a disposable cartridge system containing electrodes for connection to an extracorporeal shunt or ex vivo source of blood which provides blood chemistry analysis and calibration of the electrodes.

U.S. Pat. No. 5,057,278, issued 15 Oct. 1991 to Maxwell et al., provides a sterile loop system for calibrating sensors used to monitor various blood parameters.

SUMMARY OF THE INVENTION

Accordingly, it is a primary object of the invention to address the above-mentioned needs in the art, by providing a method for calibrating sensors used to analyze characteristics of a physiologic fluid.

It is another object of the invention to address deficiencies in the art by providing such a method which permits in situ calibration of sensors which are positioned in a physiologic line.

It is yet a further object of the invention to provide a method of performing quality control for confirming the accuracy of sensors used to analyze characteristics of a physiologic fluid.

It is still another object of the invention to provide an apparatus for calibrating a system for analyzing the characteristics of a physiologic fluid.

Additional objects, advantages and novel features of the invention will be set forth in part in the description which follows, and in part will become apparent to those skilled in the art upon examination of the following, or may be learned by practice of the invention.

In one aspect, then, a method is provided for calibrating a system for analyzing characteristics of a physiologic fluid. The method involves the use of a sensor assembly having at least one sensor responsive to a characteristic of an analyte in the physiologic fluid, wherein the sensor is in direct or indirect contact with the analyte, and further having at least one passageway which is detachably affixed to and in divertable fluid communication with a physiologic line, and a conduit by which a reference sample may be introduced into the passageway and wherein the sensor is in communication with the passageway. The method involves exposing the sensor to the reference sample, thereby producing a sensor response, and correlating the sensor response to the characteristic of the analyte in the reference sample.

In another aspect, a method is provided of performing quality control for confirming the accuracy of a system for analyzing characteristics of a physiologic fluid. The method involves the use of a sensor assembly as described above having at least one calibrated sensor responsive to a characteristic of an analyte in the physiologic fluid. The method entails exposing the calibrated sensor to the reference sample, thereby producing a sensor response, calculating from the sensor response a composition value for the analyte in the reference sample, and comparing the calculated composition value for the analyte with the known concentration of the analyte in the reference sample.

In still another aspect, an apparatus for calibrating a system for analyzing characteristics of a physiologic fluid is provided. The apparatus includes a sensor assembly as described above and further having a passageway detachably affixed to and in divertable fluid communication with a physiologic line and a conduit by which a reference sample may be introduced into the passageway, and wherein the sensor is in communication with the passageway.

BRIEF DESCRIPTION OF THE DRAWINGS

In the course of this description, reference will be made to the attached drawings, wherein like parts denote like parts throughout and wherein.

DETAILED DESCRIPTION OF THE INVENTION

Figure 1:
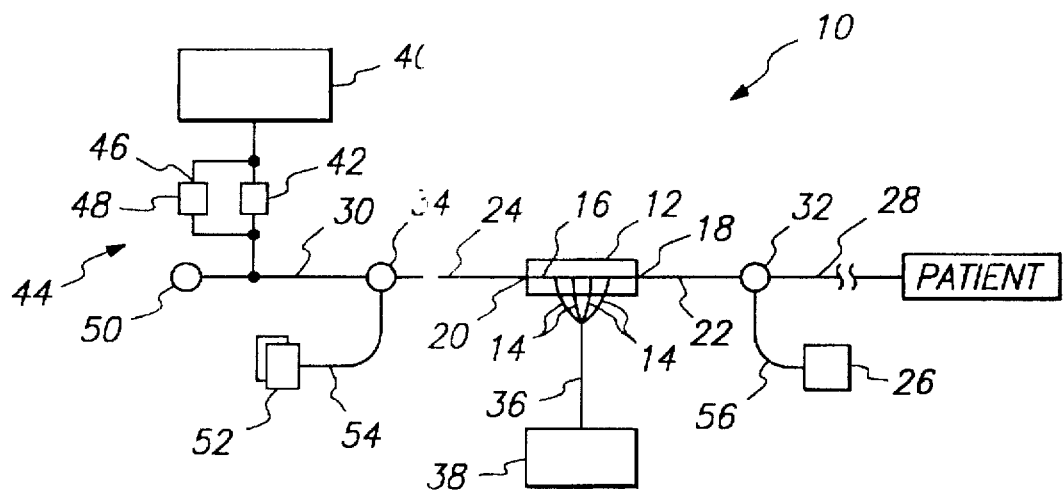
FIG. 1 is a schematic drawing of a system for monitoring characteristics of a physiologic fluid incorporating a calibration system in accordance with the teachings of the invention.

Before the present in situ sensor calibration methods and apparatus are disclosed and described, it is to be understood that this invention is not limited to specific sensor formats, reference samples or analytes as such, of course, may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a reference sample" or "a calibrant" includes more than one reference sample or calibrant, reference to "a calibration measurement" or "a quality control measurement" includes more than one such measurement, reference to "a buffer" includes mixtures of two or more buffers, and the like.

In describing and claiming the present invention, the following terminology will be used in accordance with the definitions set out below.

By "physiologic line" is intended any cannula or catheter, one end of which is intended to be situated in a body cavity, duct or vessel so as to permit the withdrawal or injection of fluids. In addition to the cannula or catheter, a physiologic line may include other tubing or conduits associated therewith. Furthermore, a cannula or catheter provides a hollow tube having an interior barrel into which a sensor may be retractably inserted.

A "reference sample" is a liquid or gaseous composition comprising a known concentration of an analyte of interest. A "standard" or "calibrant" is a reference sample used for establishing the response of a measurement system to an analyte. As such, a calibration reference is typically any of the standards of various types that indicate whether an analytical instrument is working within prescribed limits and by which adjustments may be made to the analytical measurement system to correct for any deviation from the prescribed limits.

"Calibrating" a sensor is intended to mean determining, by exposing the sensor to a reference sample, standard or calibrant, the change in sensor readout (in the case of an optical fiber the change in optical properties of the sensor), which change is associated with a known concentration of analytes in the standard. For optical fiber sensors, the optical properties of chemical sensor compositions typically involve changes in colors, color intensities, or both. A detailed discussion of the preparation and use of optical fiber sensors is provided in co-pending U.S. application Ser. Nos. 07/911,175 to Olstein and 08/074,749 to Olstein et al., both of which are incorporated herein by reference.

The term "quality assurance" intends a series of planned or systematic actions, i.e., "quality control measurements," required to provide confidence that an analytical instrument is operating within prescribed limits, thereby assuring that the results obtained from the instrument will satisfy given needs. Thus, in the context of the present invention, a "quality control measurement" is one in which a calibrated sensor is exposed to a reference sample to insure that the sensor is operating within prescribed limits. Such measurements are typically taken on a periodic basis according to a predetermined schedule, e.g., every 24 hours, and prior to, after, or both prior to and after the measurement of analyte concentrations in the physiologic fluid to determine whether the analyte measurement accurately reflects the analyte levels in the sample. If the quality control measurement indicates that the sensor no longer responds to analyte concentrations within the prescribed limits, the sensor must either be recalibrated or replaced with a substitute sensor.

The invention, together with additional features and advantages thereof, may be best understood by reference to the following description taken in connection with the illustrative drawings.

Figure 2:
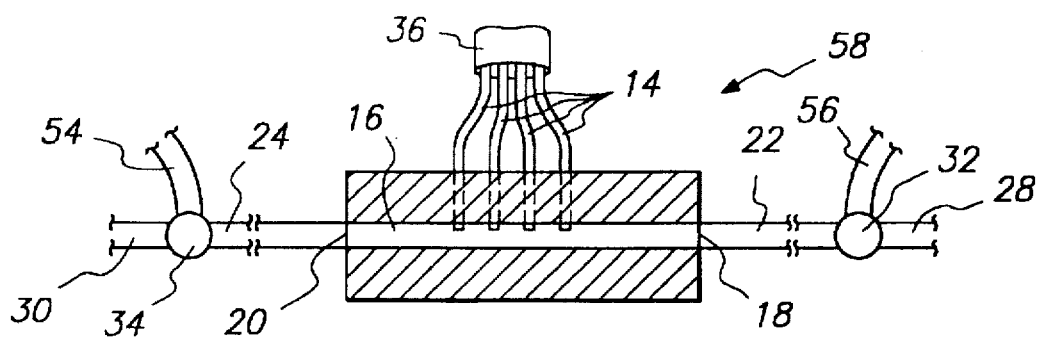
FIG. 2 is an expanded view of a portion of FIG. 1 illustrating a preferred embodiment of the sensor assembly.

With reference to FIG. 1, a system 10 is provided for calibrating sensors used to analyze chemical characteristics, for example, $pO_2$, $pCO_2$ or pH, in a physiologic fluid from a human or animal subject. The system comprises a sensor assembly 12, an expanded illustration of which assembly 58 is depicted in FIG. 2, including at least one sensor 14 in direct or indirect communication with a first passageway 16 into which the physiologic fluid, infusion medium or reference sample may be drawn or otherwise introduced. The first and second opposing ends of the passageway, respectively indicated at 18 and 20, comprise proximal and distal ports, respectively indicated at 22 and 24, through which movement of fluid into or out of the passageway is effected. Either port may serve as an inlet port, for introduction of fluid into the first passageway 16, or an outlet port, for evacuation of fluid from the passageway into a waste reservoir 26. The first passageway 16 is in fluid communication with a physiologic line 28 and an infusion medium conduit 30 by way of the ports to which are detachably affixed proximal and distal flow diversion means, indicated at 32 and 34, respectively, which direct the flow of fluid into or out of the passageway. The physiologic line 28 and the infusion medium conduit 30 are in turn detachably affixed to the proximal 32 and distal 34 flow diversion means. The output from the sensors is communicated by an appropriately sheathed communication cable 36 to an instrument 38 which acts as a sensor interface and a read-out means.

In a typical installation of the sensor assembly, the physiologic line 28 is an arterial cannula. Additional components of the system which are illustrated in FIG. 1 include a pressurized source of infusion medium 40 which is in fluid communication with the infusion medium conduit 30. Interposed between the source of infusion medium and the infusion medium conduit is an infusion medium flow restrictor 42. A fast-flush mechanism 44 is provided to bypass the flow restrictor, wherein the fast-flush mechanism includes a bypass conduit 46 and, incorporated therein, a flush valve 48. In communication with the infusion medium conduit is a pressure transducer 50 used to monitor the patient's or subject's blood pressure. These additional components are generally provided in an integrated assembly.

A source of a reference sample or calibrant 52 is provided which is in fluid communication with a reference sample conduit 54 to transfer the reference sample from the source to the passageway. This conduit is in fluid communication with flow diversion means 34, by which the reference sample may be introduced into the passageway 16 without compromising the sterility of the apparatus.

An optional waste reservoir 26 for disposing of spent reference sample is depicted in FIG. 1. The waste reservoir is in divertable fluid communication with the sensor assembly through a drain conduit 56 which is detachably affixed to a port 22 of the sensor assembly by way of a flow diversion means 32.

Referring still to FIG. 1, although the source of reference sample 32 is shown as distinct from the source of infusion medium 40, it will be recognized by the skilled practitioner that the infusion medium may serve as a reference sample as well. Furthermore, although the source of reference sample 52 is shown communicating via reference sample conduit 54 to the distal flow diversion means 34 and the waste reservoir 26 is shown communicating via drain conduit 56 to the proximal flow diversion means 32, it will be apparent that the reference sample source and the waste reservoir may be interchangeably in communication with the proximal and distal flow diversion means, respectively.

Figure 3:
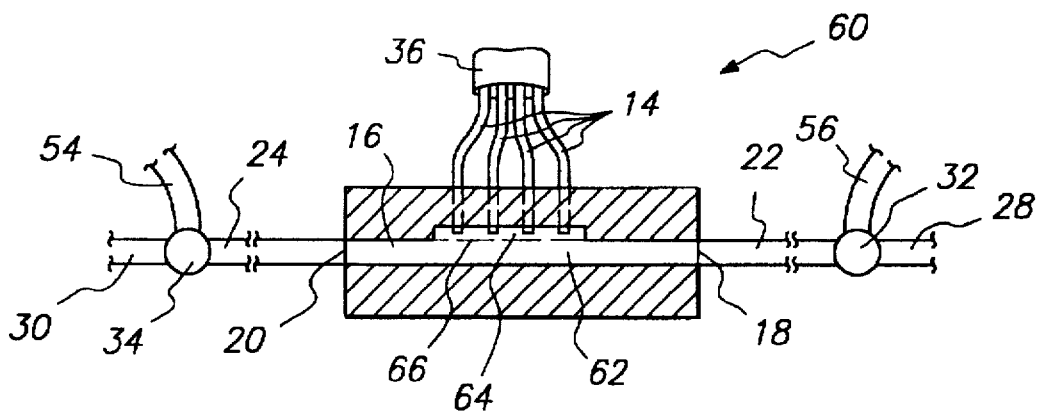
FIG. 3 is an expanded view of a portion of FIG. 1 showing another embodiment of the sensor assembly.

An alternate embodiment of the sensor assembly is illustrated in FIG. 3 and is generally indicated at 60. The sensor assembly passageway 16 may be at least partially laterally partitioned into primary and secondary chambers, indicated at 62 and 64, respectively. Interposed between the primary and secondary chambers and covering the sensors is a semipermeable membrane 66 to provide a sterile barrier separating the sensors from the sensor assembly fluid passageway. Each sensor may be respectively covered with a membrane which is selectively permeable to a particular analyte component of the reference sample and/or the physiologic fluid but impermeable to the sample and fluid themselves. Alternatively, a single, semipermeable membrane may be used to cover one or more of the sensors collectively. Such membranes which are permeable to individual gas species, e.g., $CO_2$, $O_2$, and the like, and ion-selective membranes, are well known in the art.

Figure 4:
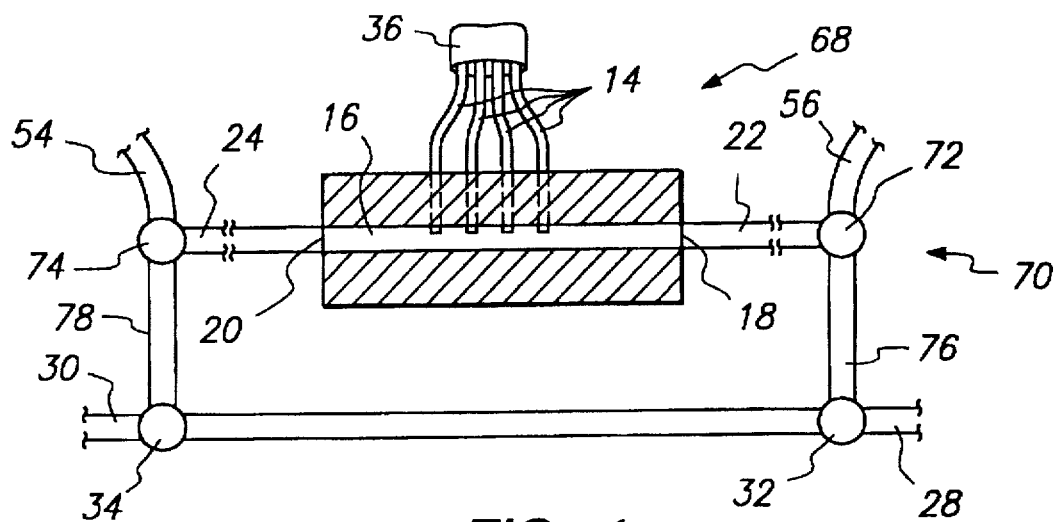
FIG. 4 is an expanded view of a portion of FIG. 1 depicting an additional embodiment of the sensor assembly.

FIG. 4 illustrates an additional embodiment of the sensor assembly. More particularly, sensor assembly 68 is shown comprising a shunt 70. The shunt and the sensor assembly are in divertable fluid communication with the physiologic line 28 by way of proximal and distal shunt flow diversion means, respectively indicated at 72 and 74, which are in divertable fluid communication with proximal flow diversion means 32 and distal flow diversion means 34 by way of proximal and distal shunt bypass conduits, respectively indicated at 76 and 78.

Figure 5:
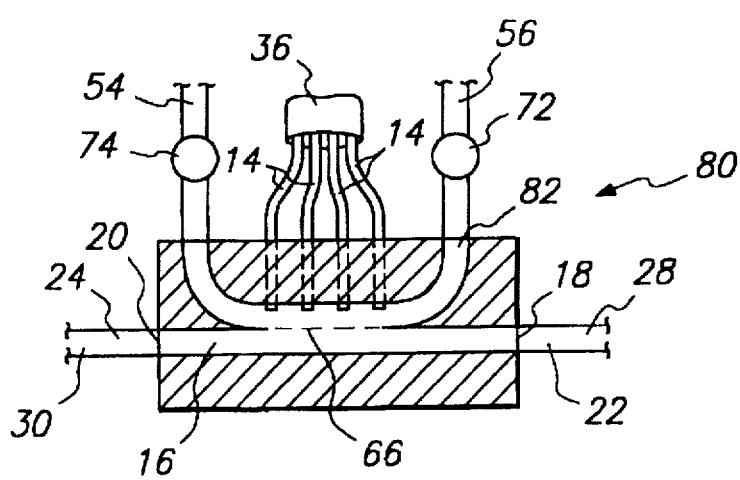
FIG. 5 is an expanded view of a portion of FIG. 1 exhibiting a further embodiment of the sensor assembly.

FIG. 5 depicts another embodiment of the sensor assembly, generally indicated at 80, in which the sensor assembly is constructed of first and second passageways, indicated at 16 and 82, respectively. Interposed between the first and second passageways, and defining the interface therebetween, is a semipermeable membrane 66 to provide a sterile barrier separating the sensors from the physiologic line. This embodiment provides the ability to constantly monitor the pressure waveform even during recalibration of the sensors or performance of quality control checks. In addition, due to the presence of the sterile barrier separating the first and second passageways, it is not necessary to use a biocompatible reference sample or to construct the sensors from biocompatible materials.

The reference sample may be biocompatible and thus made of a stable, sterile, nonpyrogenic, isotonic medium which contains known analyte concentrations. Such analytes include gases, for example, $O_2$, $CO_2$ or the like, hydrogen ion, i.e., pH, or other biological analytes the presence of which may be desirable to assess in a physiologic fluid, e.g., glucose and the like. In addition, the reference sample may contain biocompatible buffers including, for example, bicarbonate, phosphate and fluorocarbon-based synthetic buffers. Preferably, the reference sample is provided in a prepackaged and pretonometered form; however, a reference sample prepared by bedside tonometry may be used in the method and apparatus of the invention. The composition of and methods for preparing reference samples are well known in the art. Such compositions are described in, for example, U.S. Pat. Nos. 3,380,929 to Petersen, 3,681,255 to Wilfore et al. and 4,116,331 to Sorensen, the disclosures of which are incorporated by reference herein.

The reference sample may be packaged in any device or material which insures that the analyte concentrations will be maintained for the storage lifetime of the package. For example, the reference sample may be packaged in a glass ampoule, a syringe or, preferably, a flexible bag. In addition, the packaging material may be used as a storage medium for shipping and storing the sensor device until ready for use. Furthermore, a sensor calibration read-out may be taken using the packaging solution in which the sensor assembly is stored or shipped or the standard infusion medium. It is preferred that the reference sample be disposable, i.e., provided for a single-use application.

Referring again to FIG. 1, the reference sample is transferred from the source 52 to the sensor assembly passageway 16 by motive means. The motive means include a pumps, hydrostatic pressure, pressurization of the reference sample package, application of a vacuum to the opposing port of the passageway, syringe, or the like. Furthermore, the motive means may be of an impulse type, providing transfer of a quantal amount of sample into the passageway wherein the sample remains static during the calibration process, or a continuous flow type which provides dynamic exposure of sensors to the sample.

The reference sample is introduced into the passageway 16 without compromising sterility by way of a flow diversion means 34 which includes conventional three-way stopcocks, or other types of valves suitable for the purpose of the invention, and any other type of entry port, for example, a needle port, or any combination thereof. Furthermore, the flow diversion means may include a combination of more than one stopcock, entry port, or the like. Thus, in the context of the invention, it may be desirable to have both a stopcock and a needle port by which to introduce reference sample into, or remove reference sample from, the passageway 16. A standard three-way stopcock is a preferred embodiment of a flow diversion means as it functions to direct the flow of fluid from more than one source into or out of the passageway. However, the primary function of the flow diversion means may be served by any appropriate means which allows the sterile, noninvasive introduction of the reference sample into and out of the passageway.

The outlet port 22 of the passageway 16 may be divertably connected to a waste reservoir 26 by way of a drain conduit 56. The incorporation of a separate drain conduit and waste reservoir for deposit of spent reference sample depends, at least in part, on the volume of the sensor assembly passageway and, therefore, the volume of reference sample used for calibrating the sensors and the composition thereof. For example, when the device is attached to a physiologic line 28, e.g., an arterial cannula, in a neonate it would be undesirable to introduce unnecessary quantities of fluid into the patient. Consequently, an additional drain conduit 56 and waste reservoir 26 would be desirable in a neonatal installation. By contrast, if the device is attached to an in-dwelling arterial line in an adult patient, the patient will have greater tolerance for absorbing extraneous fluid volumes. In this way, the need for a drain conduit 56 or waste reservoir 26 is obviated, as the patient essentially serves as the "waste reservoir." The drain conduit 56 or waste reservoir 26 may be an additional component in divertable fluid communication with the outlet port 22 of the passageway 16, such as bag or bottle. However, depending on the age, size, condition, etc. of the subject, the drain or reservoir may be the physiologic line 28 itself or the patient. Optionally, after introduction of the reference sample into the sensor assembly passageway 16 and completion of the calibration process, the reference sample may be returned to the original storage package.

The sensors 14 which communicate with the passageway 16 are preferably blood gas or pH sensors. Optionally, a temperature monitoring means, e.g., a thermistor, may also communicate with the passageway to measure the temperature of the blood sample. However, the claimed invention is not intended to be limited to blood gas and pH sensors. The invention may also be used with sensors such as ionic sensors, glucose sensors, hemoglobin sensors, or the like. Furthermore, the invention is not limited with respect to the sensor format; sensor formats may include optical sensors, electrochemical sensors, and the like.

The sensors 14 are in direct or indirect physical, chemical or optical communication with the analyte present in the physiologic fluid or reference sample. The output of the sensors is connected by way of an appropriately sheathed communication cable 36 to a read-out means 38, which can be a display, printer or microprocessor which controls additional circuits or calculates analyte levels based on the output of the sensors.

In a typical bedside installation, for example, a sensor assembly 12 is interposed between a standard arterial catheter 28 and the conduits which lead therefrom to a pressure transducer 50 and a source of infusion medium 40. Both the proximal 22 and distal 24 ports of the sensor assembly 12 are detachably affixed to three-way luer-lock stopcocks, respectively indicated at 32 and 34. In normal operating position, in other words when the system is operated so as to monitor arterial blood pressure, the proximal stopcock 32 is open toward the patient and the distal stopcock 34 is open toward the pressure transducer 50. For calibration or quality control measurements, the stopcocks may be closed with respect to the patient and the pressure transducer 50, in which case fluid transfer may be effected from the reference sample source 52 via the reference sample conduit 54 by way of the motive means, through the sensor assembly passageway 16 and, in turn, through the outlet port stopcock 34 into the drain conduit 56 and waste reservoir 26. Normally, the pressure transducer 50 in an arterial catheter is associated with a fast-flush mechanism 44 by which infusion medium may be used to flush the catheter with heparinized saline or other appropriate buffered sterile solution. Examples of such solutions and methods of preparing same, are provided in International Publication No. WO 94/06019 (inventors Wong et al.)

Accordingly, the sensor assembly passageway 16 is flushed by opening the distal stopcock 34 toward infusion medium conduit 30 and the proximal stopcock toward the drain conduit 56 and waste reservoir 26, or the patient, and activating the fast-flush mechanism 44. The arterial line 28 is flushed in a similar manner. Alternatively, the passageway 16 and other components of the system may be flushed using a syringe motive means in, for example, a neonatal installation.

Upon initial installation and from time to time thereafter the sensors 14 in the sensor assembly 12 may be recalibrated. Often the necessity to perform a recalibration procedure is indicated by a quality control measurement which yields results which are outside predetermined measurement tolerances.

In order to calibrate the sensors 14 in communication with the sensor assembly passageway 16, the passageway and the arterial line 28, or both, are flushed with infusion medium. The proximal three-way stopcock 32 is turned off with respect to the patient and on with respect to the passageway 16 and the drain conduit 56. The distal three-way stopcock 34 is turned on with respect to the infusion medium conduit 30. Reference sample is introduced into the passageway 16 via the distal three-way stopcock 34. After the sensors 14 have equilibrated with the reference sample, a reading is taken from sensors. The reference sample is flushed from the passageway 16 with standard infusion medium and the process may be repeated with additional reference samples, thereby providing a multi-point calibration, or all stopcocks may be opened so that the distal stopcock 34 is open with respect to the passageway 16 and the pressure transducer 50 and the proximal stopcock 32 is open with respect to the passageway 16 and the patient. Additional calibration points improve the characterization of the sensor response.

A non-biocompatible reference fluid may be used to calibrate sensors 14 in a sensor assembly 12 if followed by an appropriate flushing technique that has been demonstrated to effectively remove the non-biocompatible fluid from the sensor assembly passageway 16. As such, the non-biocompatible fluid may be used for either in situ or off-line sensor calibration.

Off-line sensor calibration involves calibration or quality control measurements taken when the sensor assembly 12 is not attached to a physiologic line 28. For example, sensor calibration may be performed when the sensor assembly 12 is attached to a source of infusion medium 40 and to a source of reference sample 52 via the distal flow diversion means 34, and to a waste reservoir 26 via the proximal flow diversion means 32, but detached from a physiologic line 28. Such off-line calibration is useful to calibrate the sensors in anticipation of installing a sensor assembly 12 in a physiologic line 28. This method of calibration may also be preferred in a neonatal installation.

Figure 6:
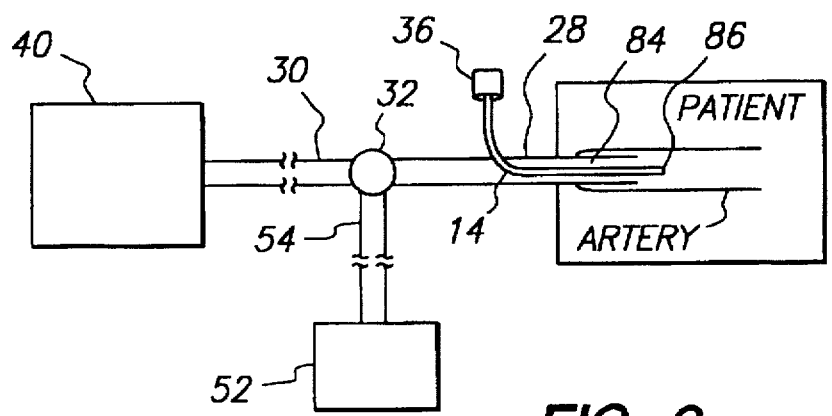
FIG. 6 is a schematic drawing of an additional embodiment of the invention.

Referring now to FIG. 6, the claimed method and apparatus may also be used to calibrate or perform quality control measurements on a sensor 14 which is retractably inserted into the barrel 84 of an in-dwelling intraarterial cannula 28. During analysis of the characteristics of arterial blood, the tip of the sensor 86, i.e., the environment-sensitive end thereof, extends beyond the intraarterial end of the cannula into the artery. In this configuration, the intraarterial cannula 28 is attached to a source of infusion medium 40 via infusion medium conduit 30 and to a source of reference sample 52 via reference sample conduit 54 by way of a flow diversion means 32, and the patient serves as the reservoir for reference sample or infusion medium. In preparation for calibration or performance of quality control checks, the sensor 14 may be retracted such that the sensor tip 86 is positioned within the barrel 84 of the cannula. Reference sample is infused into the cannula through the flow diversion means 32 such that any physiologic fluid residing in the cannula is flushed into the patient and the sensor tip 86 is exposed to reference sample. The sensor 14 can then be calibrated or a quality control measurement taken as described above.

In typical installations as depicted in, for example, FIG. 1, arterial blood gas, pH or other analyte values are monitored by drawing a sample of arterial blood into sensor assembly fluid passageway 16. After allowing the sensors 14 to equilibrate with the sample, a read-out of the sensor is recorded and the $O_2$, $CO_2$ and pH values determined. The blood may then be returned to the patient by activating the fast-flush mechanism 44 or by alternate means, e.g., by flushing the fluid passageway 16 using a syringe-flush.

System performance may be verified by conducting quality control measurements. Such measurements may be made on a periodic basis, according to a predetermined schedule, immediately prior to, after or both prior to and after monitoring arterial blood analyte values to insure that the sensors have not drifted out of calibration and will not yield erroneous result. To perform a quality control measurement, the proximal stopcock 32 is turned off with respect to the patient. The sensor system passageway 16 is flushed with flush solution by activating the fast-flush mechanism 44 on the pressure transducer 50. Reference sample is introduced into the sensor assembly fluid passageway 16 and the sensors 14 are allowed to equilibrate therewith. After taking a read-out from the sensor or sensors, a comparison is made between the $O_2$, $CO_2$ and pH values calculated based on the read-out and the known values in the reference sample. If the calculated values are outside predetermined tolerances, the system may be recalibrated.

The disclosed method and apparatus for in situ or ex vivo sensor calibration is designed to be used with blood gas ($O_2$ and $CO_2$) and pH sensors situated in an arterial line in a human or animal subject. However, utility can be extended to any type of sensor dwelling in any physiologic line, paracorporeal or extracorporeal sensors, or sensors retractably inserted in an in-dwelling intraarterial cannula. In an such configuration, the invention may be used for an initial sensor calibration, a secondary or subsequent calibration, a reference check, or a quality control check.

In addition, the invention finds utility for calibrating sensors used to analyze characteristics of other fluids, the sterility of which is of primary importance and which is potentially compromised by removing sensors for calibration prior to reinsertion. For example, the system is useful for calibrating a sensor assembly which is situated in a biological line associated with a cell culture fermenters, or the like.

Thus, the invention provides novel methods for in situ calibration of sensors situated in a physiologic line, as well as devices associated therewith. Although preferred embodiments of the subject invention have been described in some detail, it is understood that obvious variations can be made without departing from the spirit and the scope of the invention as defined by the appended claims.

We claim:

1. A method of calibrating a system for analyzing characteristics of a physiologic fluid, wherein said method comprises:

a) providing a sensor assembly located in a physiologic line, comprising (i) at least one sensor responsive to a characteristic of an analyte in the physiologic fluid and in direct or indirect contact with the analyte, and (ii) at least one passageway in communication with the sensor which is detachably affixed to and in divertable fluid communication with both the physiologic line and a conduit by which at least one reference sample having a known concentration of analyte may be introduced into the passageway;

b) exposing the sensor in the sensor assembly to the reference sample so that the sensor is in direct static contact with the reference sample, thereby producing a sensor response; and c) correlating the sensor response to the characteristic of the analyte in the reference sample.

2. The method of claim 1, wherein the reference sample comprises an infusion medium or a calibrant.

3. The method of claim 2, wherein the reference sample comprises a calibrant.

4. The method of claim 3, wherein the calibrant is a synthetic calibrant.

5. The method of claim 4, wherein the synthetic calibrant comprises a synthetic buffer.

6. The method of claim 1, further comprising, prior to step (a), providing the reference sample in premixed form.

7. The method of claim 6, wherein the reference sample is provided by premixing using tonometry.

8. The method of claim 1, further comprising exposing the sensor to two or more reference samples.

9. The method of claim 8, wherein the sensor is exposed to first and second reference samples having different known analyte concentrations.

10. The method of claim 8, wherein the reference sample comprises an infusion medium or a calibrant.

11. The method of claim 1, further comprising prior to step (b) detaching the passageway from the physiologic line.

12. A method of detecting an analyte in a physiologic fluid comprising calibrating sensors according to the method of claim 1, and further comprising exposing the sensor to the fluid and detecting the analyte in the fluid.

13. A method of performing quality control for confirming the accuracy of a system for analyzing characteristics of a physiologic fluid, wherein said method comprises:

a) providing a sensor assembly located in a physiologic line, comprising (i) at least one calibrated sensor responsive to a characteristic of an analyte in the physiologic fluid and in direct or indirect contact with the analyte and, (ii) at least one passageway in communication with the sensor which is detachably affixed to and in divertable fluid communication with both the physiologic line and a conduit by which at least one reference sample having a known concentration of analyte may be introduced into the passageway;

b) exposing the calibrated sensor to the reference sample so that the sensor is in direct static contact with the reference sample, thereby producing a sensor response;

c) calculating a composition value for the analyte in the reference sample from the sensor response; and d) comparing the calculated composition value for the analyte with the known concentration of the analyte in the reference sample.

14. The method of claim 13, wherein the reference sample comprises an infusion medium, a quality control medium or a calibrant.

15. The method of claim 14, wherein the reference sample comprises a quality control medium.

16. The method of claim 15, wherein the quality control medium is a synthetic quality control medium.

17. The method of claim 16, wherein the synthetic quality control medium comprises a synthetic buffer.

18. The method of claim 17, wherein the quality control medium is comprised of an infusion medium.

19. The method of claim 13, wherein the passageway comprises means to pass the physiologic fluid, reference sample or both through the passageway.

20. The method of claim 13, wherein the passageway includes a means to pass the reference sample.

21. The method of claim 20, wherein the means to pass the physiologic fluid, reference sample or both comprises a storage means for storing the reference sample, a motive means for delivering the reference sample from the storage means to the passageway, an introduction means for introducing the reference sample into the passageway, a drain means for removing the reference sample from the passageway and a reservoir means to contain the removed reference sample.

22. The method of claim 13, further comprising, prior to step (a), providing the quality control medium in premixed form.

23. The method of claim 22, wherein the quality control medium is provided by premixing by tonometry.

24. The method of claim 13, further comprising prior to step (b) detaching the passageway from the physiologic line.

25. A method of detecting an analyte in a physiologic fluid comprising performing quality control according to the method of claim 13, and further comprising exposing the sensor to the fluid and detecting the analyte in the fluid.

26. A method of performing quality control for confirming the accuracy of a system for analyzing characteristics of a physiologic fluid, wherein said method comprises:

a) providing a sensor assembly located in a physiologic line, comprising (i) at least one sensor responsive to a characteristic of an analyte in the physiologic fluid, calibrated according to the method of claim 1, and in direct or indirect contact with the analyte and, (ii) at least one passageway in communication with the sensor which is detachably affixed to and in divertable fluid communication with both a physiologic line and a conduit by which at least one reference sample having a known concentration of analyte may be introduced into the passageway;

b) exposing the calibrated sensor to the reference sample so that the sensor is in direct static contact with the reference sample, thereby producing a sensor response;

c) calculating a composition value for the analyte in the reference sample from the sensor response; and d) comparing the calculated composition value for the analyte with the known concentration of the analyte in the reference sample.

27. A method of detecting an analyte in a fluid comprising performing quality control according to the method of claim 26, and further comprising exposing the sensor to the fluid and detecting the analyte in the fluid.

* * * * *